United States Patent [19]

Jousson

[11] Patent Number: 5,281,137
[45] Date of Patent: Jan. 25, 1994

[54] NOZZLE HOLDER FOR BODILY CARE

[75] Inventor: Jean-Pierre Jousson, Chene-Bourg, Switzerland

[73] Assignee: Les Produits Associes LPA-Broxo S.A., Chene-Bourg, Switzerland

[21] Appl. No.: 963,909

[22] Filed: Oct. 20, 1992

[30] Foreign Application Priority Data

Nov. 4, 1991 [EP] European Pat. Off. ........ 91810852.3

[51] Int. Cl.⁵ ............................................. A61G 17/02
[52] U.S. Cl. ......................................... 433/80; 128/66
[58] Field of Search ....................... 128/66; 433/80, 81, 433/82, 84, 85

[56] References Cited

U.S. PATENT DOCUMENTS 3,540,437 11/1970 Troy ...................................... 128/66
4,442,831 4/1984 Trenary ................................ 128/66

FOREIGN PATENT DOCUMENTS 0339770 3/1990 European Pat. Off. .
3231537 1/1984 Fed. Rep. of Germany .
266506 1/1950 Switzerland .

*Primary Examiner*—John J. Wilson
*Attorney, Agent, or Firm*—Kane, Dalsimer, Sullivan, Kurucz, Levy, Eisele & Richard

[57] ABSTRACT

The nozzle holder comprises a liquid conduit and a valve (5) actuated by a control button (8) which, in the rest position, leaves free the passage of the jet of pulsed liquid towards the nozzle fixed to the nozzle holder and which, in the pressed position, closes this passage.

The valve (5) comprises a chamber (9) which is in communication with the upstream part (6) of the conduit and connected through the opening (7a) of the valve to the downstream part (7) of said conduit. This chamber (9) is delimited partially by an elastic cup (10) which can be deformed by the button (8) and which, in the rest state of the button (8), under the effect of its own elasticity and of the pressure of the liquid, remains moved away from the opening (7a) of the valve and is completely inactive while, under the action of the pressed button, it covers the opening (7a) of the valve (5) to block the passage of the liquid. In this blocked state, the part of the cup (10) surrounding the opening (7a) of the valve is deformable under the effect of the pulsations of the liquid such that said chamber undergoes a periodic expansion, damping these liquid pulsations.

5 Claims, 3 Drawing Sheets

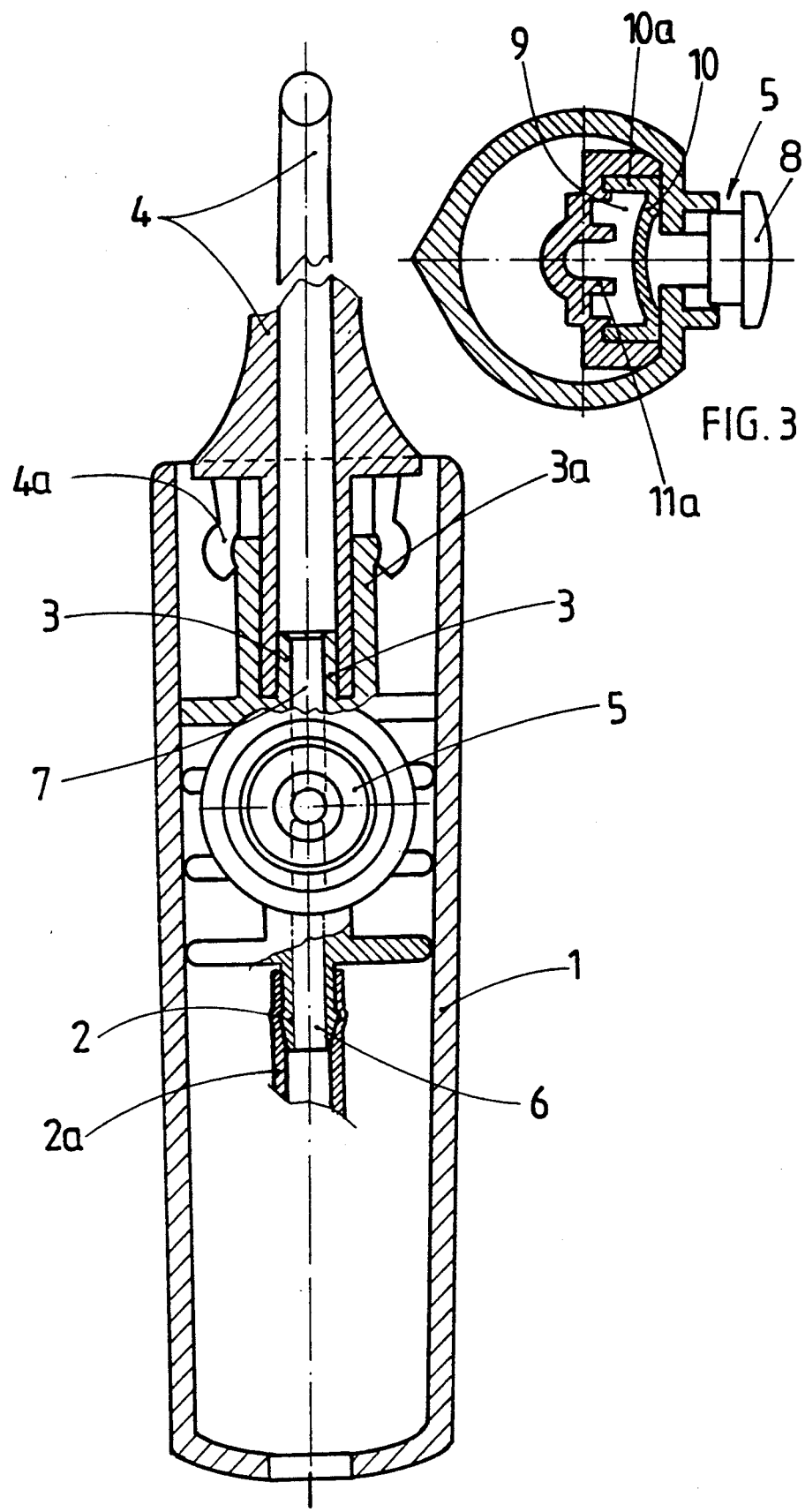

5,281,137

NOZZLE HOLDER FOR BODILY CARE

FIELD OF THE INVENTION

The invention relates to a nozzle holder for bodily, in particular oral, care, by means of a jet of pulsed liquid, formed by a casing/handle comprising a liquid conduit between an inlet connection and an outlet connection intended for the fixing of a nozzle, as well as a valve installed in this conduit and comprising a control button which, in the rest state, carries out the opening of the valve and which can be pressed in order to reduce the passage of liquid and, in its final pressed position, close the valve.

Nozzle holders of this type, which are fed by a hydraulic pump by means of a pipe, make it possible for the user temporarily to interrupt the passage of the liquid by simply pressing the button which is arranged on the periphery of the casing/handle. This measure makes it possible in particular for the user to change the nozzle without it being necessary to stop the pump and then have to set it in operation again, which is much more practical.

PRIOR ART

A nozzle holder as mentioned above is known, for example, from the patents CH-A 657265 (DE-A3231537) and comprises a valve which simply interrupts the passage of the liquid when the button is pressed. This interruption is brought about either by compression of the conduit constituted by a flexible internal pipe, or by a stop member which is displaced inside the conduit. This interruption of the passage of the pulsed liquid has the disadvantage of loading the pump and its motor. In fact, the column of liquid which is situated between the piston of the pump and the stop member of the valve is enclosed between rigid walls and, under the effect of the pulsations, it can practically only yield via poor joints or by virtue of the compression of any air bubbles. In certain cases, the pump itself can jam which risks damaging it as well as the motor. In any case, in the closure position of the valve, the inlet conduit is subjected to great shocks which are due to the pulsations and which make the entire apparatus vibrate. Ultimately, this can even cause damage to the pipe or to another part.

SUMMARY OF THE INVENTION

The aim of the present invention is to create a valve such that, in the closure state, the pump and the motor are relieved by a damping of the pressure shocks due to the pulsations.

By these measures, in the closure state of the valve, the column of liquid enclosed between the piston and the closed valve can oscillate, making said chamber expand, which dampens the pulsations.

According to a preferred embodiment of the invention, the chamber is delimited on the side of the button by a cup and on the opposite side by an internal wall of the casing, the central zone of which comprises the opening of the valve, the internal end of the button being situated in contact with the central zone of the external face of the cup which, in the rest state, bears against this button and against rigid faces of the casing, and the greater part of which, in the closure position, is moved away from said faces; by virtue of this moving away of the cup, the latter is free to be expanded by the pulsations. Preferably, the cup has the form of a pot, the rim of which is held in a groove of the internal wall of the casing, which comprises in its central zone a collar surrounding said opening of the valve and serving as a seat for the cup in the closure position of the valve.

BRIEF DESCRIPTION OF THE DRAWINGS

The invention will be described with the aid of an embodiment with reference to the attached drawings.

FIG. 2 is a longitudinal cross-section of the nozzle holder according to FIG. 1 turned at 90° about its longitudinal axis.

FIG. 3 is a section along the line III in FIG. 1.

DESCRIPTION OF THE PREFERRED EMBODIMENT(S)

Figure 1:
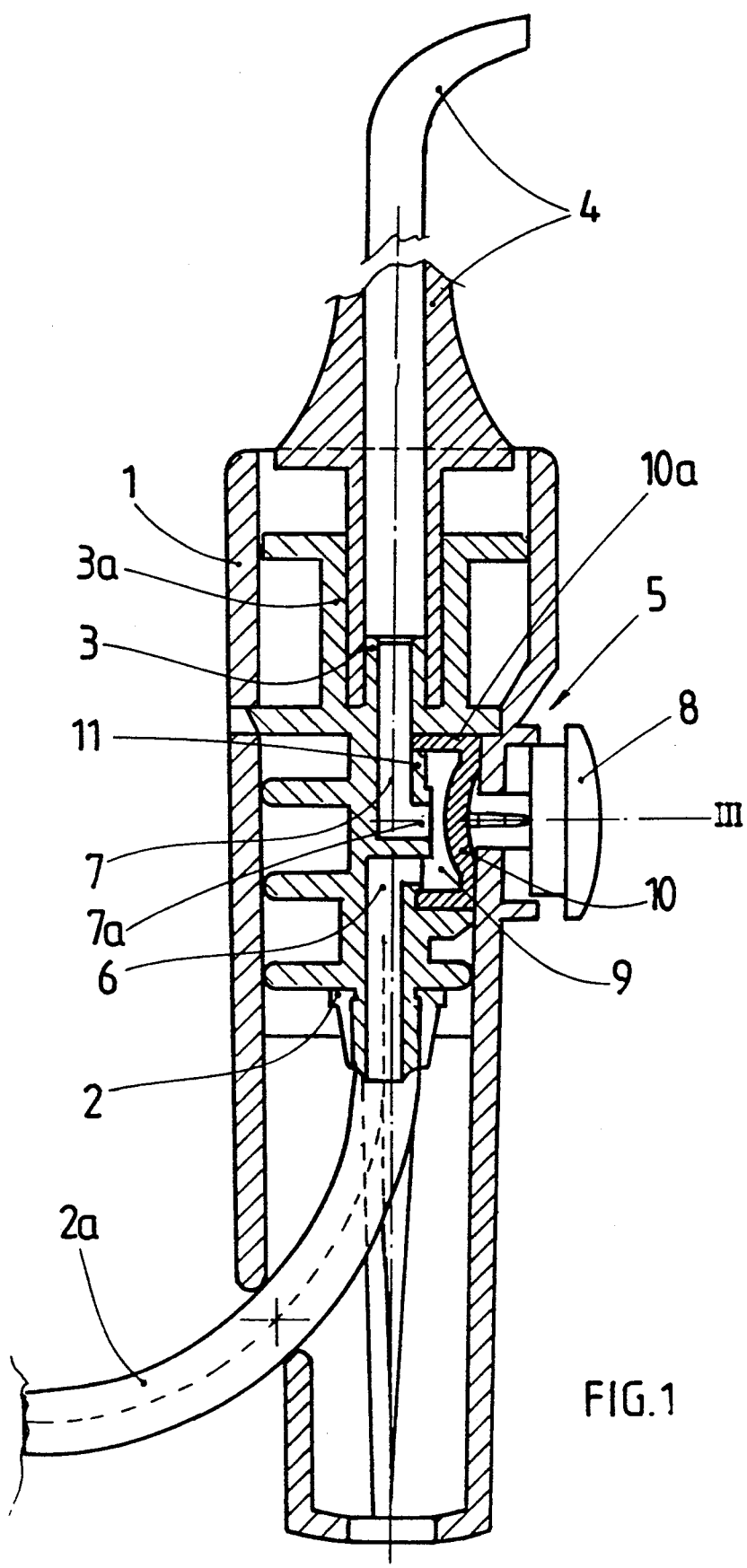
FIG. 1 is a longitudinal cross-section of the nozzle holder, on which a nozzle is fixed.

In FIGS. 1 and 2, a nozzle holder 1 can be seen, the inlet connection 2 of which is connected by means of a pipe 2a to a hydraulic pump (not shown) which is driven by a motor (also not shown). This pump creates liquid pulsations of a frequency of, for example, 50 Hz. A nozzle 4 is fixed on the outlet connection 3 by means of internal projections 3a of the nozzle holder and elastic tongues 4a (FIG. 2) at the lower end of the nozzle 4.

The nozzle holder has the form of a casing/handle 1 which comprises an internal liquid conduit 6, 7 arranged between the inlet connection 2 and the outlet connection 3.

Between these two connections 2, 3, there is situated a valve 5 comprising a control button 8 which is arranged on the periphery of the casing and is displaceable radially by pressure, a chamber 9 in permanent communication with the upstream part 6 of the conduit, as well as an elastic cup 10. The chamber 9 is delimited on the side of the button by said cup 10 which has the form of a pot, and on the other side by an internal wall 11 of an internal body of the casing/handle 1. This wall 11 has, in its zone situated facing the button 8, a collar 11a (FIGS. 3 to 5) surrounding the opening 7a of the valve which is connected to the downstream part 7 of said conduit, said collar 11a forming the seat of this valve.

It can be seen that the chamber 9 is mainly constituted by an annular space surrounding said collar 11a. Moreover, this internal wall 11 comprises a groove 12 (FIGS. 4 and 5) which surrounds said annular space and in which the rim 10a of the elastic cup 10 is held.

Figure 4:
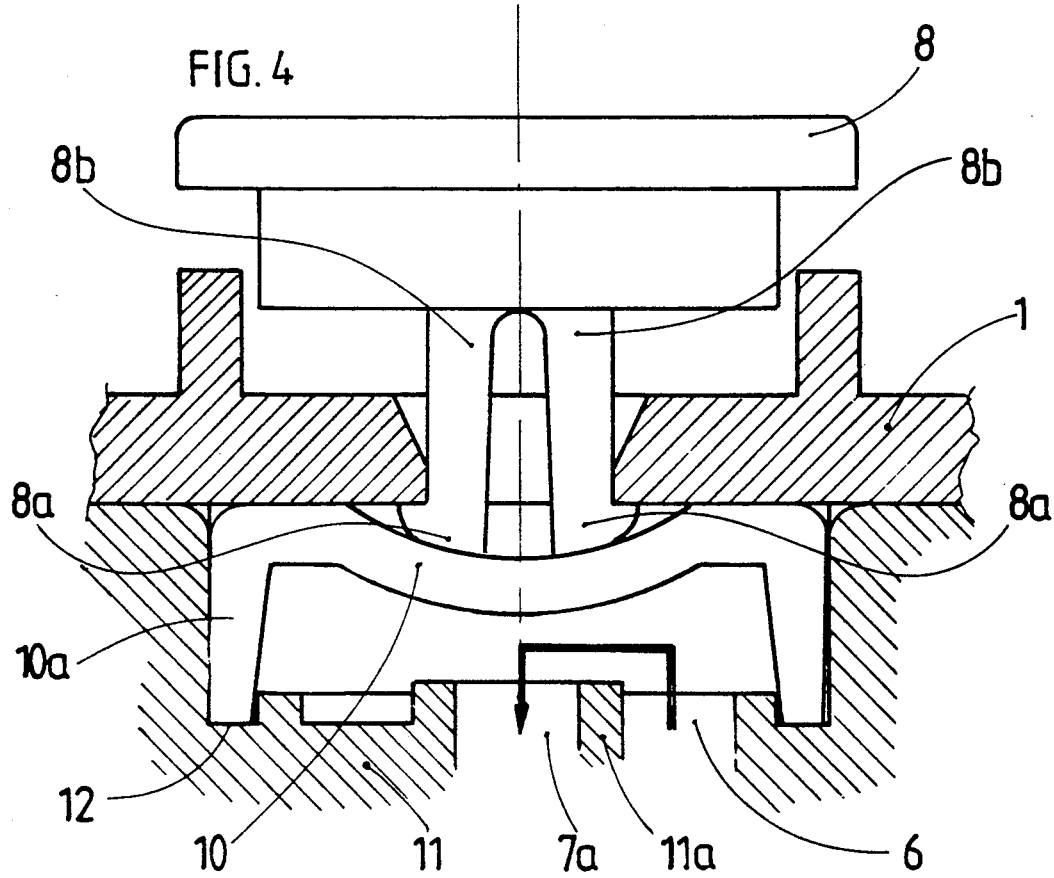
FIG. 4 is a diagrammatic view of the valve alone, in the rest state, therefore in open position.

As illustrated in FIGS. 1 and 4, in the rest state of the button 8, thus if the latter is not pressed, the cup 10, under the effect of its own elasticity and of the pressure of the liquid, bears completely against the rounded internal end 8a of the button 8 (FIG. 4), holding the latter in the rest position, and against the internal faces of the peripheral and internal walls of the casing/handle 1, and, under these conditions, said cup 10 remains completely inactive and acts like a rigid element during use of the nozzle holder for treatment by a jet of liquid which passes through according to the arrow in FIG. 4. In the example considered, the internal part of the button 8 is split and forms two arms 8b (FIG. 4), the rounded ends 8a of which are in the form of hooks which, in the rest state, bear against the internal wall of the casing/handle and limit the displacement of the button towards the outside.

Figure 5:
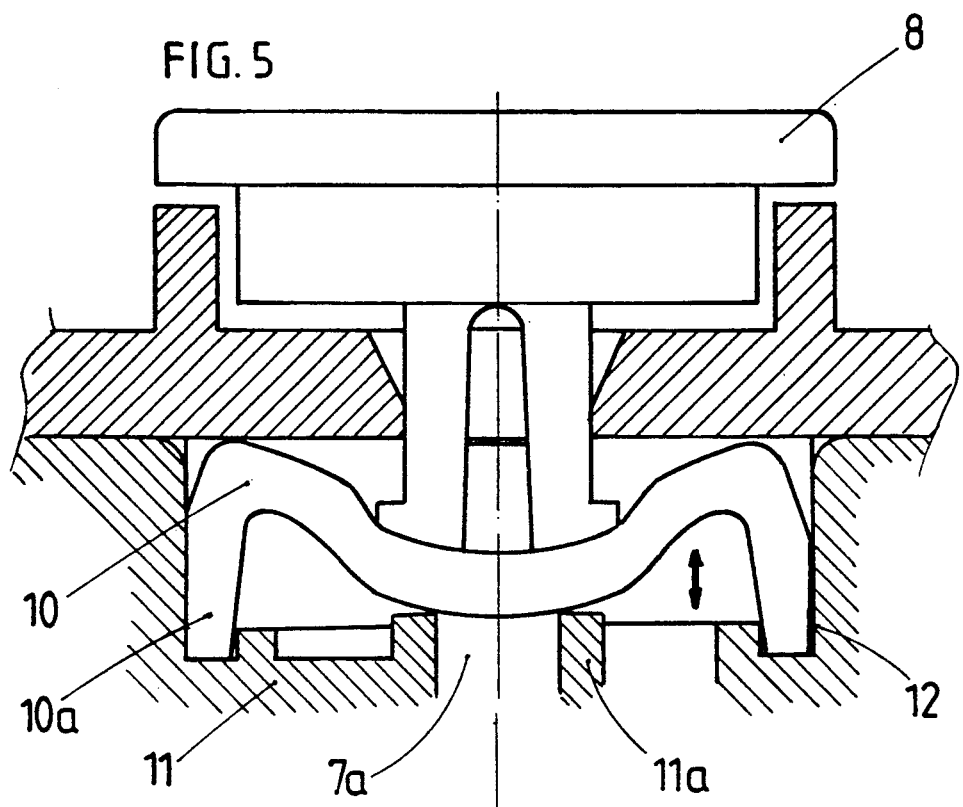
FIG. 5 represents a similar view to FIG. 4 with the valve in the closed position.

If the user wishes to interrupt momentarily the passage of the liquid, he presses the button 8, which leads, as shown in FIG. 5, to the deformation and the displacement of the cup 10 and consequently the progressive closure of the passage of the liquid into the opening 7a of the valve until complete blocking of this passage. In this blocked position as illustrated in FIG. 5, the central zone of the cup is pressed against the collar 11a while the greater part of the cup 10 surrounding this central zone is moved away from the internal faces of the casing/handle, which allows it to be deformed freely under the effect of the pulsations of the liquid, symbolized by the double arrow in FIG. 5, and the chamber 9 can therefore undergo a periodic expansion, damping these pulsations of the liquid and consequently relieving the pump and the motor. If the button 8 is released, under the effect of its elastic return force and of the pressure of the liquid in the chamber 9, the cup 10 moves away from the collar 11a and is again applied against the internal faces of the casing, pushing the button 8 into its rest position.

In the example considered, the body of the valve 5 and the internal conduits 6 and 7 with the inlet and outlet connections 2 and 3 are formed by a single piece which is inserted and fixed in the casing/handle 1. This piece moreover also comprises projections 3a for fixing the nozzle 4.

The invention is not limited to the embodiment which has just been described but numerous variants could be envisaged without departing from the spirit of the invention.

I claim:

1. A nozzle holder for bodily, in particular oral, care, by means of a jet of pulsed liquid, comprising a handle (1), an inlet connection (2) and an outlet connection (3) for coupling with a nozzle (4), a liquid conduit between the inlet connection and the outlet connection and having an upstream part (6) and a downstream part (7), a valve (5) installed in this conduit and being movable between a rest state and final pressed closed position, a valve seat defining an opening (7a) communicating with the downstream part (7), a control button (8) coupled with the valve and adapted to be digitally depressed to press the valve towards the pressed closed position, which, in the rest state, permits the opening of the conduit and which can be pressed in order to reduce the conduit and the passage of liquid therein and, which in its final pressed closed position, closes the conduit, said valve (5) defining a chamber (9) which is in communication with the upstream part (6) of said conduit and connected through the opening (7a) of the valve seat to the downstream part (7) of said conduit, the valve being an elastic, cup (10) which can be deformed by the button (8) said chamber (9) being delimited partially by an elastic cup (10), and which, in the rest state, under the effect of its own elasticity and of the pressure of the liquid in the chamber remains moved away from the opening (7a) of the valve seat and while, under the action of the depressed button, the cup deforms to cover the opening (7a) of the valve (5) to block the passage of the liquid to the downstream part of the conduit, the cup having a peripheral part surrounding the opening (7a) of the valve, the peripheral part of the cup defining a peripheral part of the chamber and being elastically deformable under the effect o the pulsations of the liquid such that said peripheral part of the chamber undergoes a periodic expansion to dampen these liquid pulsations when the valve is in its final pressed closed position.

2. The nozzle holder as claimed in claim 1, wherein the handle (1) includes an internal wall (11) and opposed rigid faces and wherein said chamber (9) is delimited on the side of the button (8) by said cup (10) and on the opposite side by the internal wall (11) defining the valve seat and said opening (7a) of the conduit, the button (8) having an internal end (8a), the cup having an external face having a central zone, the internal end (8a) of the button being in contact with the central zone of the external face of the cup (10) which, in the rest state, bears against this button and against the rigid faces of the handle, and the greater part of the external face of the cup in the pressed closed position, is moved away from said faces.

3. The nozzle holder as claimed in claim 1, wherein the handle has a groove (12), said cup (10) has the form of a pot and has a rim (10a) of which is held in the groove (12).

4. The nozzle holder as claimed in claim 1, wherein the seat and the upstream and downstream parts (6, 7) with the inlet and outlet connections (2, 3) are formed from a single piece which is inserted and fixed into the handle (1), this piece also comprising a projection (3a) for attaching the nozzle (4).

5. The nozzle holder as claimed in claim 1, wherein, the handle has an internal wall and the button (8) has an internal part which is split, forming two arms (8b), the ends of which are rounded and formed as hooks which, in the rest state, bear against the internal wall of the handle and limit the displacement of the button towards the outside of the handle.

* * * * *